(12) United States Patent
Onishi et al.

(10) Patent No.: US 7,238,175 B2
(45) Date of Patent: *Jul. 3, 2007

(54) DISPOSABLE DIAPER

(75) Inventors: Kazuaki Onishi, Kagawa-ken (JP);
Yasushi Sayama, Kagawa-ken (JP);
Hiroyuki Tanji, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 349 days.

This patent is subject to a terminal disclaimer.

(21) Appl. No.: 10/082,211

(22) Filed: Feb. 26, 2002

(65) Prior Publication Data

US 2002/0120248 A1    Aug. 29, 2002

(30) Foreign Application Priority Data

Feb. 27, 2001  (JP) ............................. 2001-052651

(51) Int. Cl.
*A61F 13/495*  (2006.01)
*A61F 13/494*  (2006.01)
*A61F 13/539*  (2006.01)
*A61F 13/496*  (2006.01)

(52) U.S. Cl. .............................. 604/385.24; 604/385.19
(58) Field of Classification Search ................ 604/347, 604/348, 385.01, 385.101, 385.19, 385.21, 604/385.23, 385.24–385.3, 397–398
See application file for complete search history.

(56) References Cited

U.S. PATENT DOCUMENTS 3,995,638 A  * 12/1976  Schaar ........................ 604/389
4,938,755 A  *  7/1990  Foreman ................. 604/385.27
5,527,302 A  *  6/1996  Endres et al. ........... 604/385.21
5,558,660 A     9/1996  Dreier
5,897,544 A  *  4/1999  Ronnberg ............... 604/385.19
6,121,510 A     9/2000  Sauer
6,217,563 B1 *  4/2001  Van Gompel et al. .................... 604/385.101
6,248,098 B1 *  6/2001  Sayama .................. 604/385.28
6,506,185 B1 *  1/2003  Sauer et al. ............ 604/385.01
6,638,260 B2 * 10/2003  Mishima ................. 604/385.01

(Continued)

FOREIGN PATENT DOCUMENTS

EP           0 998 891 A2     5/2000

(Continued)

OTHER PUBLICATIONS

Translation of JP 8-196565.*

*Primary Examiner*—K. M. Reichle
(74) *Attorney, Agent, or Firm*—Clark & Brody

(57) ABSTRACT

A disposable diaper includes a basic absorbent batt structure and a supplementary absorbent batt structure placed thereon. An elastic member is provided between the two batt structures so as to transversely cross them. Contraction of the elastic member causes opposite side edge regions of the two batt structures to be pulled nearer to a longitudinal center line thereof. This results in a zone of the former batt structure underlying a distal end portion of the latter batt structure to curving downward with respect to a lower surface of the latter batt structure while the distal end portion of the latter batt structure curves upward with respect to a body facing surface of the basic absorbent batt structure. The curving of the batt structures forms a pocket opening from a front waist region toward a crotch region of the disposable diaper.

8 Claims, 10 Drawing Sheets

U.S. PATENT DOCUMENTS

2002/0099351 A1* 7/2002 Onishi et al. .......... 604/385.19
2002/0111594 A1* 8/2002 Onishi et al. ................ 604/379
2005/0203477 A1* 9/2005 Mishima et al. ....... 604/385.28
2005/0228358 A1* 10/2005 Mishima et al. ....... 604/385.19

FOREIGN PATENT DOCUMENTS

| JP | 8196565 A | * | 8/1996 |
| WO | 99/63921 | | 12/1999 |
| WO | WO 9963921 A1 | * | 12/1999 |

* cited by examiner

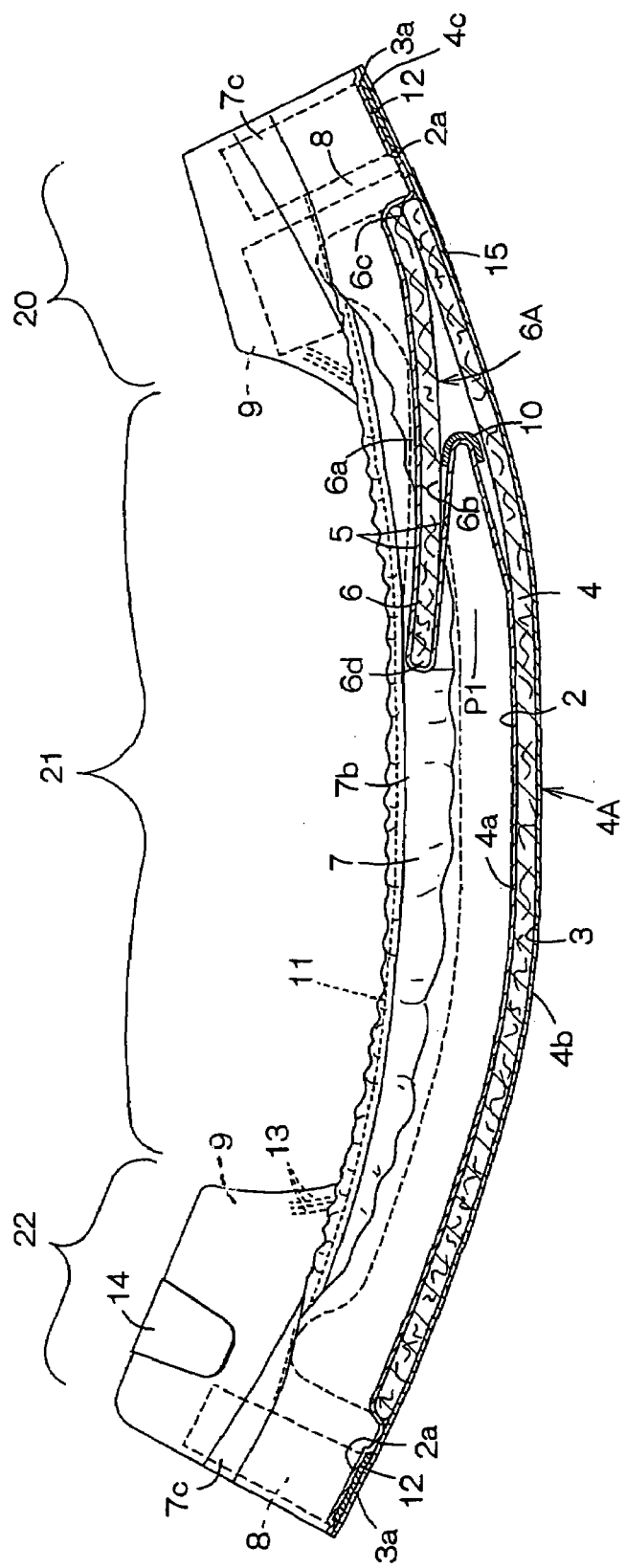

DISPOSABLE DIAPER

BACKGROUND OF THE INVENTION

This invention relates to a disposable diaper for absorption and containment of body wastes and the like.

Japanese Patent Application A No. 1996-196565 discloses a disposable diaper comprising a liquid-pervious topsheet, a liquid-impervious backsheet and a liquid-absorbent core interposed between these sheets. The core consists of an upper layer core and a lower layer core. The upper layer core consists of, in turn, a front core extending from a front waist region toward a crotch region and a rear core extending from a rear waist region toward the crotch region. In this diaper, a rear end of the front core and a front end of the rear core are spaced from each other in a longitudinal direction of the diaper by a given dimension, and the topsheet covering the upper surface of the upper core is folded back along the rear end of the front core and the front end of the rear core toward the lower layer core and tucked between the upper core and lower layer core.

In this diaper of well known art, a pocket is formed between the front core and the lower layer core so as to open from the front waist region toward the crotch region and another pocket is formed between the rear core and the lower layer core so as to open from the rear waist region toward the crotch region. In this way, these pockets can receive feces.

However, the diaper disclosed in the above-cited Application has no arrangement for positively spacing the rear end of the front core and front end of the rear core upward from the lower layer core, so the rear end of the front core as well as the front end of the rear core are apt to come in contact with the lower core. Correspondingly, it is difficult for the pockets to be sufficiently opened. With this diaper of well known art, the quantity of feces cannot be easily received within these pockets. The excessive quantity of feces may cling to a wearer's skin.

SUMMARY OF THE INVENTION

It is an object of this invention to provide a disposable diaper improved so as to ensure that pockets are sufficiently opened and thereby prevent any quantity of feces from clinging to wearer's skin.

According to this invention, there is provided a disposable diaper comprising a basic absorbent batt structure and at least one supplementary absorbent batt structure. The basic absorbent batt structure has a liquid-pervious body faceable surface and a liquid-impervious garment faceable surface, and a front waist region, a rear waist region and a crotch region. The supplementary absorbent batt structure has a liquid-pervious body facing surface and an opposite lower surface, and a proximal end portion lying in the front waist region and a distal end portion lying in the crotch region, and being placed upon the body facing surface of the basic absorbent batt structure. The proximal end portion lies in the front waist region while the distal end portion lies in the crotch region.

An elastic member under an extension in a transverse direction extends in the transverse direction across the diaper along a zone of the distal end portion of the supplementary absorbent batt structure rather adjacent its proximal end portion and has its transversely opposite end regions substantially connected to the side edge regions of the basic and supplementary absorbent batt structures. Contraction of the elastic member causes the side edge regions of the supplementary absorbent batt structure to be pulled nearer to a longitudinal center line of the diaper so that the distal end portion of the supplementary absorbent batt structure curves so as to delineate a circular arc which is convex upward with respect to the body facing surface of the basic absorbent batt structure and consequently a pocket opening from the front waist region toward the crotch region is formed between the basic and supplementary absorbent batt structures.

BRIEF DESCRIPTION OF THE DRAWINGS

FIG. 10 is a cross-sectional view taken along the line X—X in FIG. 9.

DETAILED DESCRIPTION OF THE PREFERRED EMBODIMENTS

Details of a disposable diaper according to this invention will be more fully understood from the description on an open-type diaper adopted as an exemplary case given hereunder in reference to the accompanying drawings.

Figure 1:
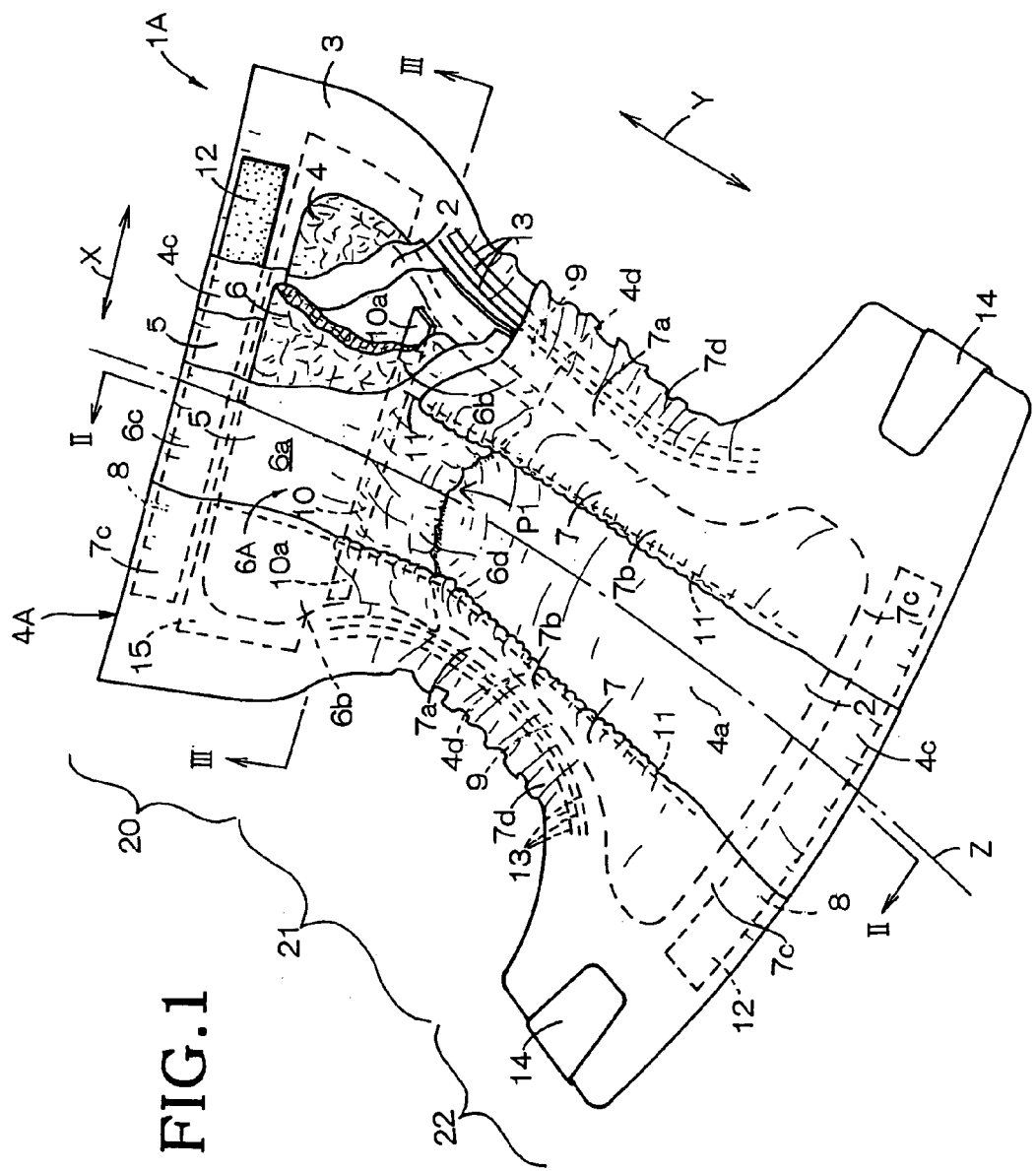
FIG. 1 is a partially cutaway perspective view showing a diaper as viewed from a side of the topsheet.
Figure 2:
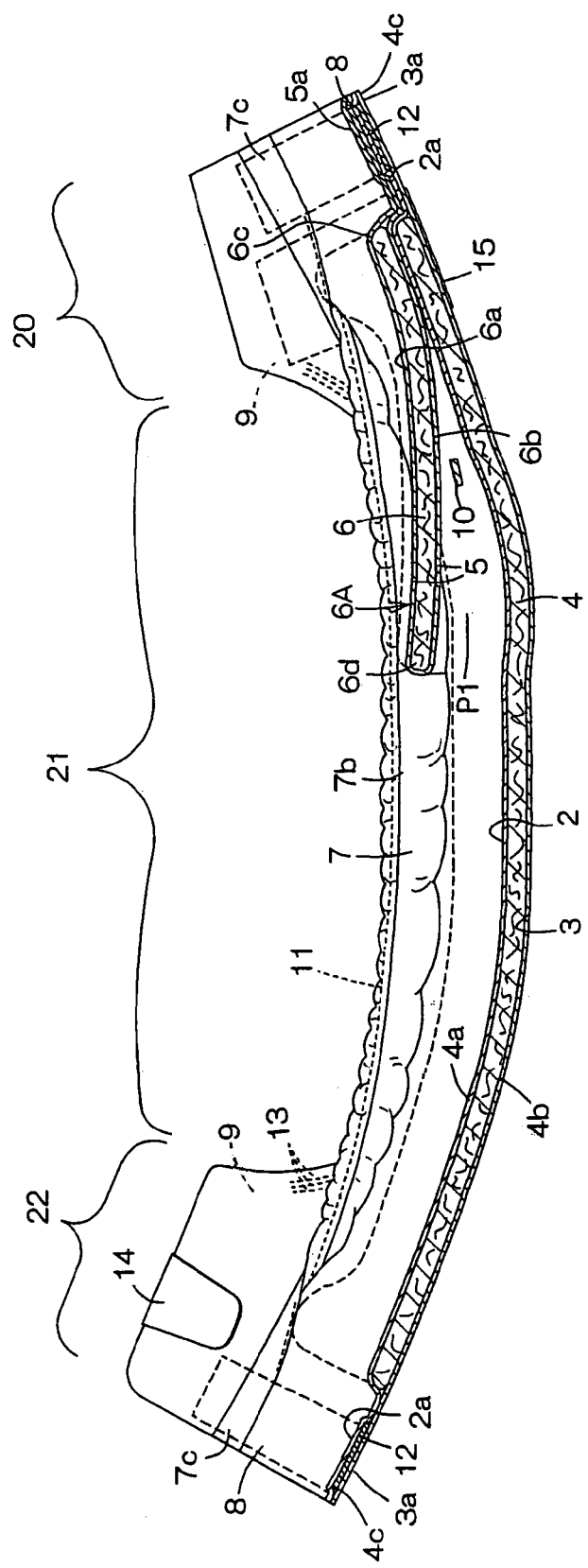
FIG. 2 is a cross-sectional view taken along the line II—II in FIG. 1.
Figure 3:
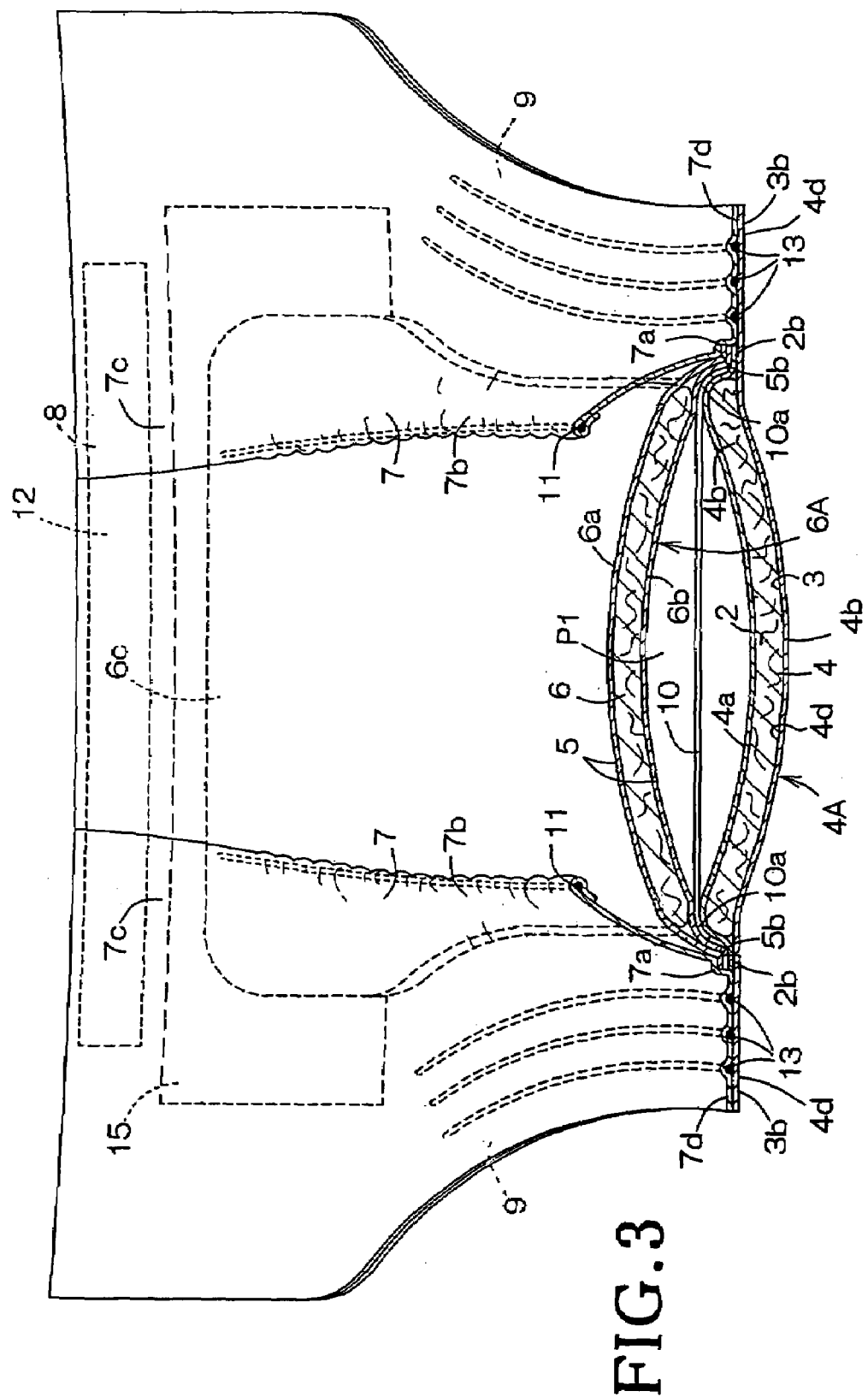
FIG. 3 is a cross-sectional sectional view taken along a line III—III in FIG. 1.
Figure 4:
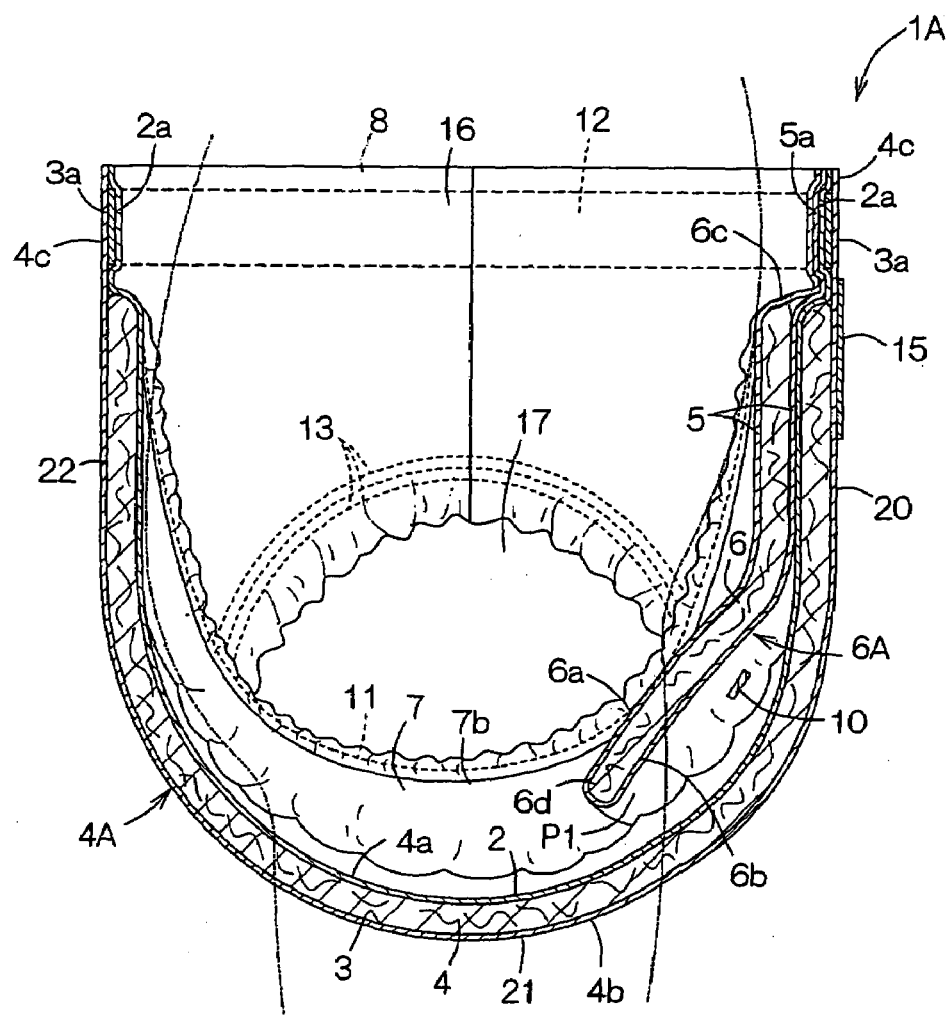
FIG. 4 is a perspective view and a partially cross-sectional view showing the diaper of FIG. 1 as put on the wearer's body with front and rear waist regions connected to each other.

FIG. 1 is a partially cutaway perspective view showing a diaper 1A as viewed from the side of a topsheet 2 and partially broken away, FIG. 2 is a cross-sectional view taken along the line II—II in FIG. 1, FIG. 3 is a cross-sectional view taken along the line III—III in FIG. 1 and FIG. 4 is a perspective view and a partially cross-sectional view showing the diaper 1A of FIG. 1 as put on a wearer's body with front and rear waist regions 20, 22 connected to each other. In FIG. 1, a transverse direction is indicated by an arrow X and a longitudinal direction is indicated by an arrow Y.

The diaper 1A comprises a liquid-pervious topsheet 2, a liquid-impervious backsheet 3, a liquid-absorbent first core 4 disposed between these two sheets 2, 3, a liquid-absorbent second core 6 wrapped by a liquid-pervious covering sheet 5, and substantially liquid-impervious barrier cuffs 7. The topsheet 2, the backsheet 3 and the first core 4 constitute a basic absorbent batt structure 4A and the covering sheet 5 and the second core 6 constitute a supplementary batt structure 6A. The diaper 1A is composed, in the longitudinal direction, of a front waist region 20, a rear waist region 22 and a crotch region 21 extending between the front and rear waist regions 20, 22.

The batt structure 4A has a body faceable surface 4a defined by the topsheet 2 and a garment faceable surface 4b defined by the backsheet 3 and longitudinally opposite end portions 4c transversely extending in the front and rear waist regions 20, 22 and transversely opposite side edge portions 4d longitudinally extending between these two end portions 4c. A pair of end flaps 8 transversely extends between the respective end portions 4c and the associated end portions of the core (4). A pair of side flaps 9 longitudinally extends between the side edge portions 4d and the associated side edge portion of the core (4). In the crotch region 21, the side flaps 9 curve inwardly in the transverse direction of the diaper 1A so as to delineate circular arcs, respectively.

The batt structure 6A has a body faceable surface 6a defined by an upper portion of the covering sheet 5 and an opposed lower surface 6b defined by a lower portion of the covering sheet 5 and is placed upon the body facing surface 4a of the batt structure 4A and extends from the front waist region 20 toward the crotch region 21. The batt structure 6A has a proximal end portion 6c placed upon the side edge portion 4c of the batt structure 4A in the front waist region 20, a distal end portion 6d lying in the crotch region 21 and transversely opposite side edge portions 6e placed upon the respective end portion 4c of the batt structure 4A and longitudinally extending between these two end portions 6c, 6d.

The one end 4c of the batt structure 4A and the proximal end portion 6c of the batt structure 6A are joined to each other by means of the topsheet 2 and the covering sheet 5. The transversely opposite side edge portions 4d, 6e of the batt structure 4A, 6A, respectively, are joined together also by means of the topsheet 2 and the covering sheet 5.

A first elastic member 10 under an extension in the transverse direction extends across the diaper 1A along a zone of the distal end portion 6d of the batt structure 6A rather adjacent its proximal end portion 6c while this first elastic member 10 lies between the topsheet 2 and the upper portion of covering sheet 5 and has its transversely opposite end portions 10a lying on the side edge portions 4d, 6e of the batt structure 4A, 6A, respectively, joined to the topsheet 2 and the covering sheet 5 by means of hot melt adhesive (not shown). Subsequently, the transversely opposite end portions 10a of the first elastic member 10 are connected to the side edge portions 4d of the batt structure 4A and to the side edge portions 6e of the batt structure 6A.

Contraction of the first elastic member 10 causes the side edge portions 4d of the batt structure 4A and the side edge portions 6e of the batt structure 6A to be pulled nearer to a longitudinal center line Z of the diaper 1A. Consequently, the zone of the batt structure 4A underlying the distal end portion 6d of the batt structure 6A curves so as to delineate a circular arc which is convex downward with respect to the lower surface 6b of the batt structure 6A while the distal end portion 6d of the batt structure 6A curves so as to delineate a circular arc which is convex upward with respect to the body faceable surface 4a of the batt structure 4A. Between the batt structure 4A, 6A, a pocket P1 with an opening from the front waist region 20 toward the crotch region 21 is formed.

Each of the cores 4, 6 comprises a mixture of fluff pulp and super-absorbent polymer particles or a mixture of fluff pulp, super-absorbent polymer particles and thermoplastic synthetic resin fibers compressed to a desired thickness. Preferably, the cores 4, 6 are entirely covered with a tissue paper in order to prevent the polymer particles from leaking out and/or to prevent the cores 4, 6 from being deformed. The polymer particles may be selected from the group consisting of starch-, cellulose- and synthetic-polymer particles.

The barrier cuffs 7 lie on the side flaps 9 and extend in the longitudinal direction. The cuffs 7 respectively have proximal edge portions 7a extending in the longitudinal direction immediately outside the associated side edge portion of the core 4 of the batt structure 4A, distal edge portions 7b extending in parallel to the proximal edge portions 7a and normally biased to rise up above the body faceable surface 4a of the batt structure 4A and longitudinally opposite fixed end portions 7c lying in the front and rear waist regions 20, 22 and collapsed inwardly in the transverse direction of the diaper 1A. The cuffs 7 respectively have the proximal edge portions 7a joined to the side flaps 9 and the fixed end portions 7c joined to the end flaps 8.

The cuffs 7 further include lateral portions 7d extending transversely outward from the respective proximal edge portions 7a. The distal edge portions 7b are provided with elastic members 11 extending in the longitudinal direction and bonded under extension to the respective distal edge portions 7b. The elastic members 11 are covered with parts of the respective distal edge portions 7b.

The diaper 1A curves in the longitudinal direction with the topsheet 2 inside and contraction of the elastic members 11 causes the distal edge portions 7b of the cuffs 7 to rise up above the body faceable surface 4a of the batt structure 4A. In the front waist region 20, the distal edge portions 7b of the cuffs 7 rise up above the body faceable surface 6a of the batt structure 6A.

The end flaps 8 are provided with belt-like elastic members 12 extending in the transverse direction and bonded under extension to the respective end flaps 8 so as to be operatively associated with a waist-hole. In the crotch region 21, the side flaps 9 are respectively provided with a plurality of elastic members 13 extending in the longitudinal direction and bonded under extension to the respective side flaps 9 so as to be operatively associated with leg-holes.

In the rear waist region 22, proximal end portions of tape fasteners 14 are joined to the respective side flaps 9 so that these tape fasteners 14 may extend transversely inward. The tape fasteners 14 are coated on their distal end portions with adhesive (not shown). In the front waist region 20, the backsheet 3 is provided on its outer surface with a rectangular target tape strip 15 formed of a plastic film and serving as a landing zone for the tape fasteners 14.

In the end flaps 8, longitudinally opposite end portions 2a of the topsheet 2 as well as longitudinally opposite end portions 3a of the backsheet 3 extend longitudinally outward beyond the longitudinally opposite ends of the core 4 and are overlaid and joined to each other as will be best seen in FIG. 2. Longitudinal end regions 5a of the covering sheet 5 forming the proximal end portion 6c of the batt structure 6A are overlaid and joined to each other as well as to the associated end portions 2a of the topsheet 2. The longitudinally opposite fixed end portions 7c of the cuffs 7 are joined to the respective end portions 5a of the covering sheet 5. The elastic members 12 operatively associated with the waist-hole are interposed between the end portions 2a of the topsheet 2 and the end portions 3a of the backsheet 3, respectively, and joined to these end portions 2a, 3a.

In the side flaps 9, transversely opposite side edge portions 2b of the topsheet 2 forming parts of the side edge portions 4d of the batt structure 4A and transversely opposite side edge portions 3b of the backsheet 3 extend transversely outward of the associated side edge portion of the core 4. The transversely opposite side edge portions 3b as well as the lateral portions 7d of the cuffs 7 extend transversely outward beyond the side edge portions 2b of the topsheet 2, as will be best seen in FIG. 3. The side edge portions 2b and the side edge portions 3b are overlaid and joined to each other. The side edge portions 3b and the lateral portions 7d are overlaid and joined to each other.

Transversely opposite side edge portions 5b of the covering sheet 5 forming the side edge portions 6e of the batt structure 6A are overlaid and joined to each other, interposed between the side edge portions 2b of the topsheet 2 and the proximal edge portions 7a of the cuffs 7, and joined to the side edge portions 2b and the proximal edge portions 7a. The elastic members 13 operatively associated with the leg-holes are interposed between the side edge portions 3b of the backsheet 3 and the lateral portions 7d of the cuffs 7 and joined to these portions 3b, 7d.

To wear the diaper 1A, the side flaps 9 in the rear waist region 22 are placed upon the outer side of the side flaps 9 in the front waist region 20 and the distal end portions of the respective tape fasteners 14 are anchored on the target tape strip 15 by means of adhesive so as to connect the front and rear waist regions 20, 22 to each other. With the diaper 1A having the front and rear waist regions 20, 22 connected to each other in this manner, a waist-hole 16 and a pair of leg-holes 17 are defined, as shown in FIG. 4.

With the diaper 1A put on a wearer's body, the batt structure 4A is normally in a state curving downward with respect to the lower surface 6b of the batt structure 6A while the distal edge portion 6d of the batt structure 6A is normally in a state curving upward with respect to the body facing surface 4a of the batt structure 4A. In this way, the pocket P1 is sufficiently opened to ensure a desired high level of capacity of this pocket P1 for feces.

Even when a large quantity of loose passage or watery feces is discharged on the diaper 1A in the crotch region 21 and spreads on the topsheet 2 toward the front waist region 20, most of such feces can be received by the pocket P1 and not migrate onto the batt structure 6A. This diaper 1A therefore can reliably prevent, in the front waist region 20, any quantity of feces from clinging to a wearer's skin. After such feces have been received in the pocket P1, a water-content thereof is absorbed and retained by the batt structures 4A, 6A and a solid-content thereof is retained in the pocket P1.

Preferably an absorbing capacity for bodily discharges per unit area of the batt structure 6A is greater than that of the batt structure 4A. Of bodily discharges, urine is discharged onto the batt structure 6A and then absorbed thereby. The batt structure 6A has the absorbing capacity for bodily discharges higher than that of the batt structure 4A so that most of urine can be absorbed and retained in the batt structure 6A and does not mix with feces within the pocket P1.

The distal edge portions 7b of the respective cuffs 7 are elastically biased to rise up and to form barriers against bodily discharges. In this way, the diaper 1A ensures to prevent bodily discharges from leaking sideways beyond the side flaps 9.

Figure 5:
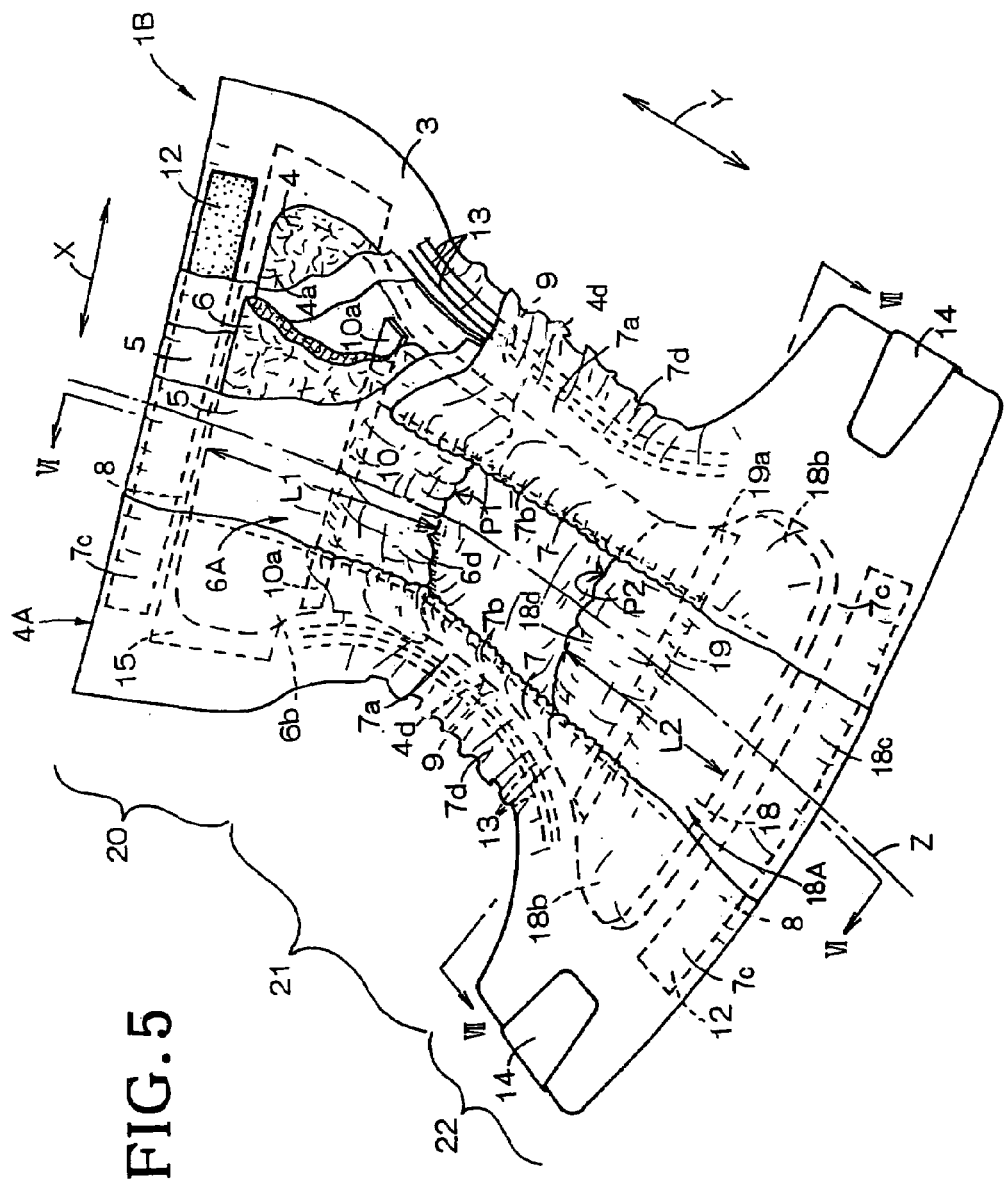
FIG. 5 is a partially cutaway perspective view showing another embodiment of the diaper.
Figure 6:
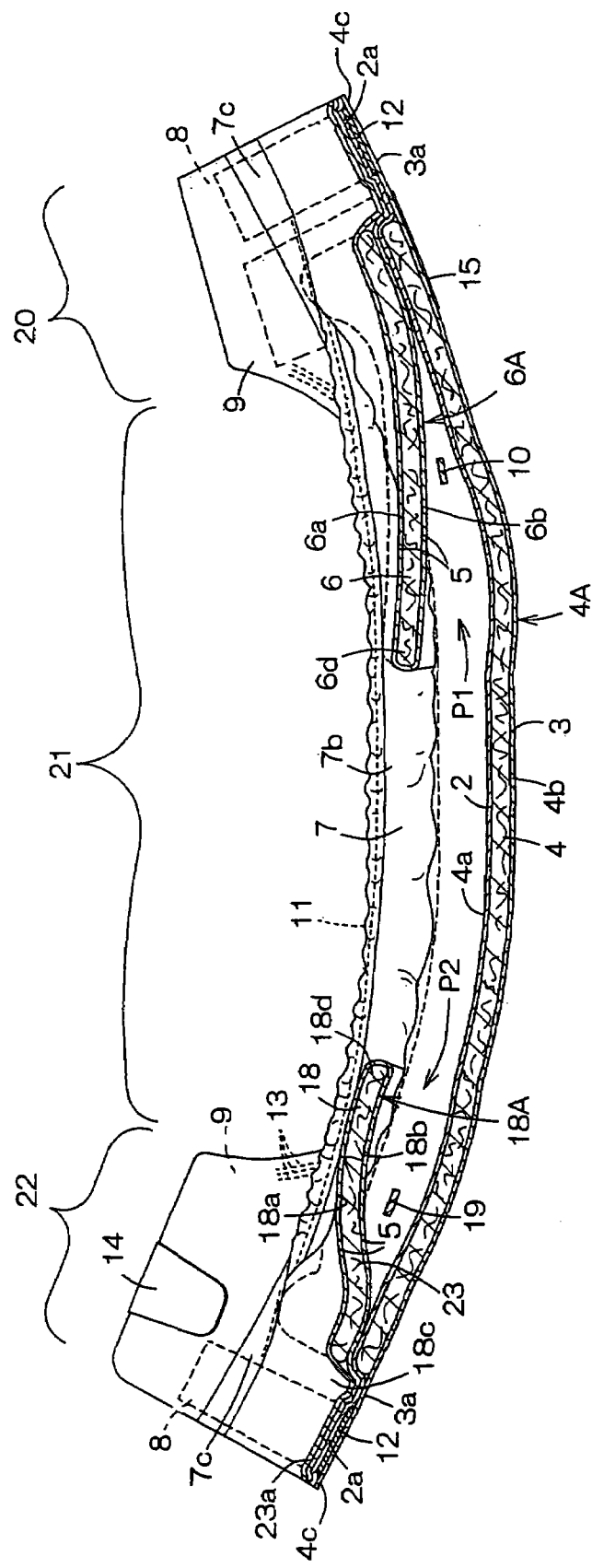
FIG. 6 is a cross-sectional view taken along the line VI—VI in FIG. 5.
Figure 7:
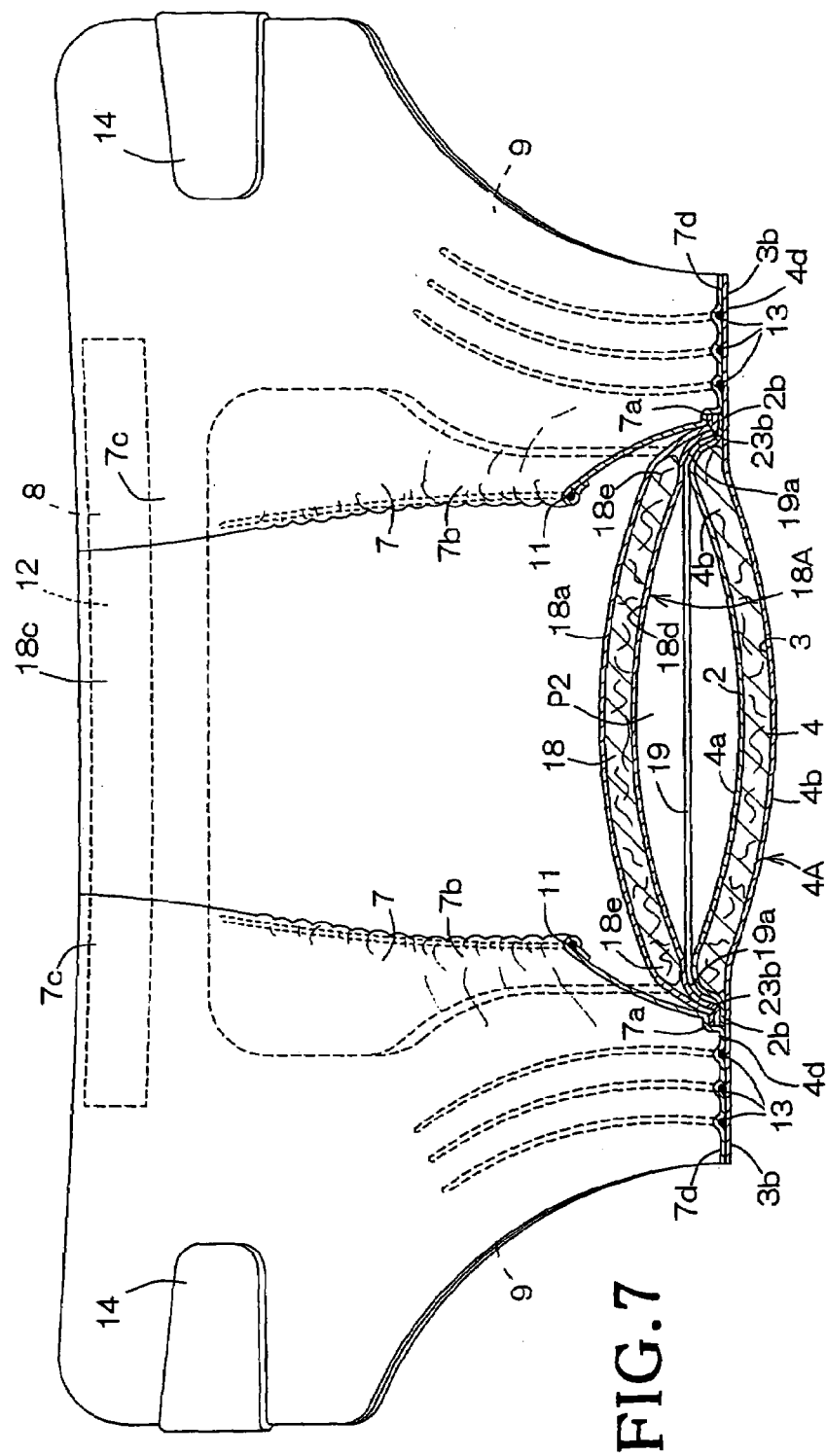
FIG. 7 is a cross-sectional view taken along the line VII—VII in FIG. 5.
Figure 8:
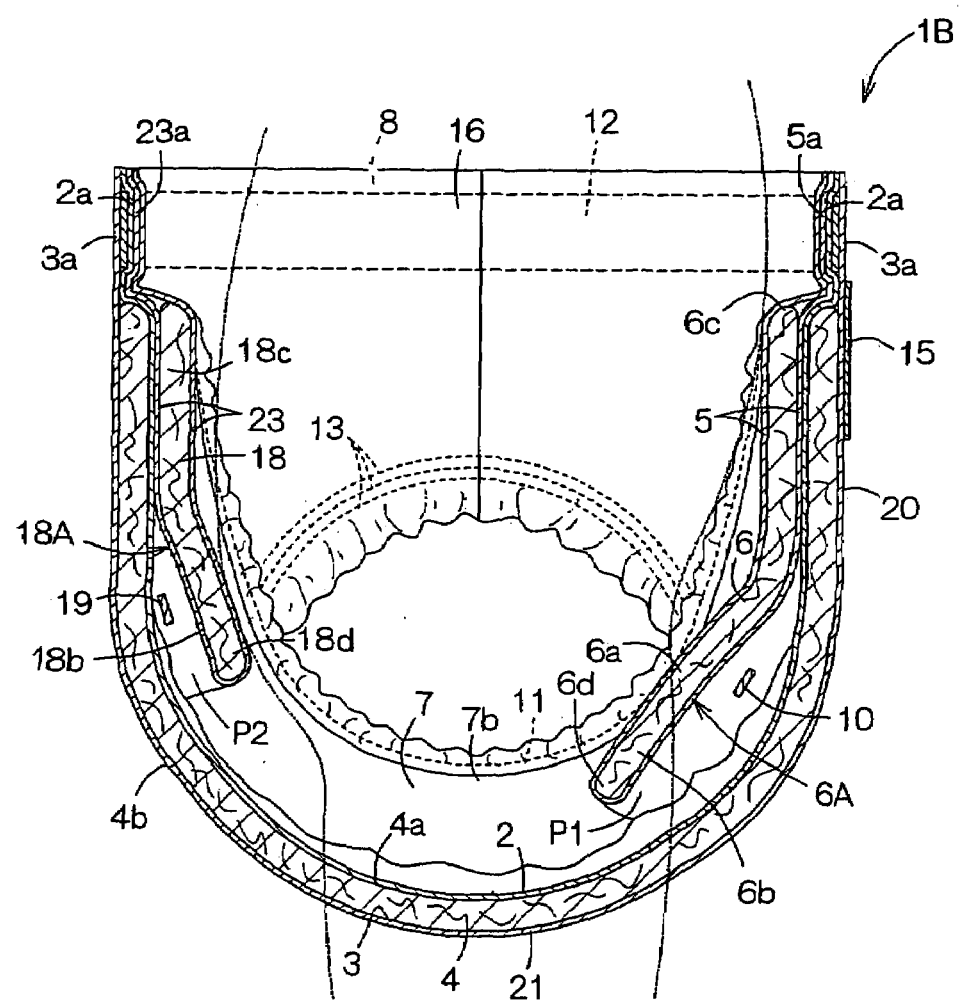
FIG. 8 is a perspective view and a partially sectional view showing the diaper of FIG. 5 partially in a sectional view as put on the wearer's body with the front and rear waist regions connected to each other.

FIG. 5 is a partially cutaway perspective view showing another embodiment 1B of the diaper, FIG. 6 is a cross-sectional view taken along the line VI—VI in FIG. 5, FIG. 7 is a cross-sectional view taken along the line VII—VII in FIG. 5 and FIG. 8 is a perspective view and a partially cross-sectional view showing the diaper 1B of FIG. 5 as put on a wearer's body with the front and rear waist regions 20, 22 connected to each other. In FIG. 5, a transverse direction is indicated by an arrow X and a longitudinal direction is indicated by an arrow Y. The diaper 1B shown in FIG. 5 is distinguished from the diaper 1A shown in FIG. 1 in that the diaper 1B includes a second supplementary absorbent batt structure 18A.

The batt structure 18A lies on the side of the body faceable surface 4a of the batt structure 4A and extends from the rear waist region 22 toward the crotch region 21. The batt structure 18A has a proximal end portion 18c lying in the rear waist region 22 and placed upon the end portion 4c of the batt structure 4A, a distal end portion 18d lying in the crotch region 21 and transversely opposite side edge portions 18e placed upon the respective side edge portions 4d of the batt structure 4A and extending in the longitudinal direction between the end portions 18c, 18d. The batt structure 18A has a body facing surface 18a and an opposite lower surface 18b covered with a covering sheet 23. The liquid pervious covering sheet 23 is folded back along the distal end portion 18d.

One of the longitudinally opposite end portions 4c of the batt structure 4A and the proximal end portion 18c of the batt structure 18A are joined together by means of the topsheet 2 and the covering sheet 23. The transversely opposite side edge portions 4d, 18e of the batt structure 4A, 18A are joined together also by means of the topsheet 2 and the covering sheet 23.

A second elastic member 19 under a extension in the transverse direction extends across the diaper 1B along a zone of and the distal end portion 18d of the batt structure 18A rather adjacent its proximal end portion 18c while this second elastic member 19 lies between the topsheet 2 and an upper portion of covering sheet 23 and has its transversely opposite end portions 19a lying on the side edge regions 4d, 18e of the batt structure 4A, 18A, respectively, joined to the topsheet 2 and the covering sheet 23 by means of hot melt adhesive (not shown). Subsequently, the transversely opposite end portions 19a of the second elastic member 19 are connected to the side edge portions 4d of the batt structure 4A and to the side edge portions 18e of the batt structure 18A.

The side edge portions 4d, 18e of the batt structure 4A, 18A are pulled nearer to the longitudinal center line Z. As a result, the zone of the batt structure 4A underlying the distal end portion 18d of the batt structure 18A curves so as to delineate a circular arc which is convex downward with respect to the lower surface 18b of the batt structure 18A while the distal end portion 18d of the batt structure 18A curves so as to delineate a circular arc which is convex upward with respect to the body faceable surface 4a of the batt structure 4A. Between the batt structure 4A, 18A, a pocket P2 opening from the rear waist region 22 toward the crotch region 21 is formed.

A third core 18 of the batt structure 18A comprises a mixture similar to those forming the first and second cores 4, 6 and is compressed to a desired thickness. Preferably, the third core 18 is entirely covered with a tissue paper.

A length L1 by which the batt structure 6A extends from the front waist region 20 to the crotch region 21 is larger than a length L2 by which the batt structure 18A extends from the rear waist region 22 to the crotch region 21. The distal end portions 6d, 18d of the batt structure 6A, 18A, respectively, are spaced from each other in the crotch region 21 so that the body faceable surface 4a of the batt structure 4A defined by the topsheet 2 is partially exposed between the distal end portions 6d, 18d. The body faceable surface 4a of the batt structure 4A is exposed in a zone of the crotch region 21 put aside to the rear waist region 22.

The end portions 23a of the covering sheet 23 forming a part of the proximal end portion 18c of the batt structure 18A are overlaid and joined to each other and joined also to the associated end portion 2a of the topsheet, as will be best seen in FIG. 6. The fixed end portions 7c of the respective cuffs 7 are joined to the respective end portions 23a of the covering sheet 23.

As will be seen in FIG. 7, the side edge portions 23b of the covering sheet 23 forming the respective side edge portions 18e of the batt structure 18A are overlaid and joined to each other. These side edge portions 23b are disposed between the respective side edge portions 2b of the topsheet 2 and the respective proximal edge portions 7a of the cuffs 7 and joined to the side edge portions 2b and proximal edge portions 7a.

The batt structure 4A curves so as to delineate a circular arc which is convex downward with respect to the lower surface 18b of the batt structure 18A while the distal end portion 18d of the batt structure 18A curves so as to describe a circular arc which is convex upward with respect to the body faceable surface 4a of the batt structure 4A. The pocket P2 formed between these batt structure 4A, 18A is largely opened. This diaper 1B allows feces to be received not only by the pocket P1 but also by the pocket P2. In this way, the diaper 1B ensures the receiving capacity for feces higher than that in the diaper 1A shown in FIG. 1 and thereby reliably prevents any significant quantity of feces from leaking sideways beyond the end flaps 8 in the rear waist region 22. With this diaper 1B, there is no anxiety that any quantity of feces might cling to a wearer's skin in the front waist region 20 as well as in the rear waist region 22.

Figure 9:
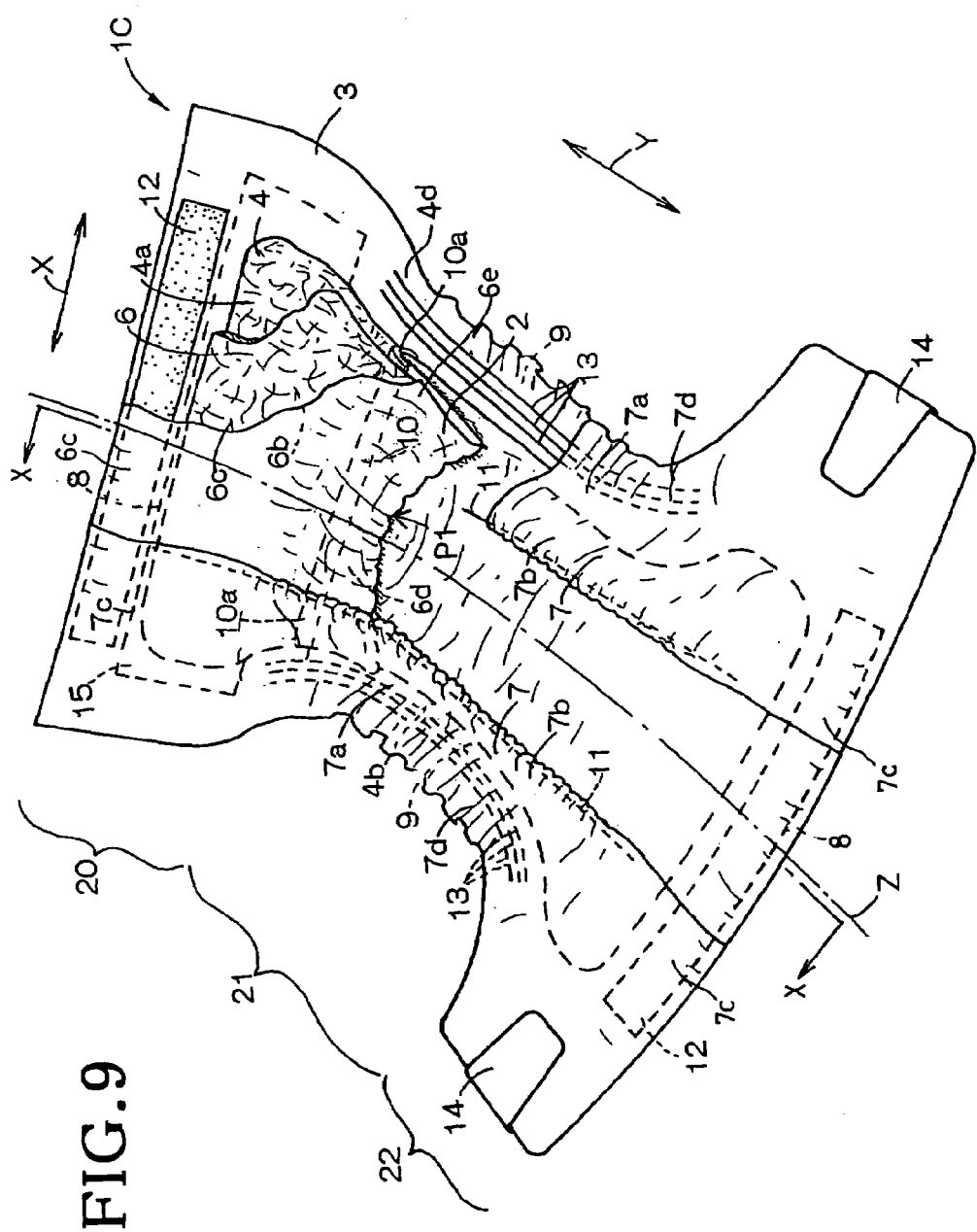
FIG. 9 is a partially cutaway perspective view showing still another embodiment of the diaper.

FIG. 9 is a partially cutaway perspective view showing still another embodiment 1C of the diaper and FIG. 10 is a cross-sectional view taken along the line X—X in FIG. 9. In FIG. 9, a transverse direction is indicated by an arrow X and a longitudinal direction is indicated by an arrow Y. The diaper 1C shown in FIG. 9 is distinguished from the diaper 1A shown in FIG. 1 in the arrangement as will be described below.

In this diaper 1C, the cores 4, 6 of the batt structure 4A, 6A are interposed between the top- and backsheets 2, 3. The topsheet 2 is folded back along the distal end portion 6d toward the side of the lower surface 6b of the batt structure 6A and tucked between the body faceable surface 4a of the batt structure 4A and the lower surface 6b of the batt structure 6A.

The body faceable surface 6a of the batt structure 6A, a part of the lower surface 6b of the batt structure 6A, and the body faceable surface 4a of the batt structure 4A are defined with the topsheet 2.

The first elastic member 10 under an extension in the transverse direction extends across the diaper 1C between the proximal end portion 6c and a free end of the distal end portion 6d of the batt structure 6A while the elastic member 10 lies between the first core 4 and the second core 6 and has its transversely opposite end portions 10a joined to the side edge portions 4d, 6e of the batt structures 4A, 6A by means of hot melt adhesive (not shown) while this intermediate portion extending between the transversely opposite end portions 10a is joined to the topsheet 2 by means of hot melt adhesive (not shown).

The zone of the batt structure 4A underlying the distal end portion 6d of the batt structure 6A curves so as to delineate a circular arc which is convex downward with respect to the lower surface 6b of the batt structure 6A while the distal end portion 6d of the batt structure 6A curves so as to delineate a circular arc which is convex upward with respect to the body faceable surface 4a of the batt structure 4A. Between the batt structure 4A, 6A, the pocket P1 opening from the front waist region 20 toward the crotch region 21 is formed.

The topsheet 2 and the liquid-pervious sheet 5 may be formed of a hydrophilic fibrous nonwoven fabric or a finely porous plastic film. The backsheet 3 may be formed of a hydrophobic fibrous nonwoven fabric, a liquid-impervious plastic film, two-layers of hydrophobic fibrous nonwoven fabric laminated with each other or a composite sheet consisting of a hydrophobic fibrous nonwoven fabric and a plastic film bonded to this hydrophobic fibrous nonwoven fabric. The barrier cuffs 7 may be formed of a hydrophobic fibrous nonwoven fabric.

It is also possible to form the backsheet 3 and the leak barrier cuffs 7 using a composite nonwoven fabric consisting of a highly water resistant fibrous nonwoven fabric made between melt blown process which is sandwiched by two layers of fibrous nonwoven fabric having a good strength and flexibility made by spun bond method.

Nonwoven fabric used herein may be selected from the group including those obtained by spun lace-, needle punch-, melt blown-, thermal bond-, spun bond-, chemical bond- and air through-processes. Component fibers of such nonwoven fabric may be selected from the group consisting of polyolefin-, polyester- and polyamide-based fibers and core-sheath type or side-by-side type conjugated fibers of polyethylene/polypropylene or polyethylene/polyester.

Bonding of the top- and backsheets 2, 3, the liquid-pervious sheet 5 and the barrier cuffs 7 as well as attachment of the cores 4, 6, 18, and the elastic members 10, 11, 12, 13 to these top- and backsheets 2, 3 and liquid-pervious sheet 5 may be carried out using hot melt adhesive or welding technique such as heat-sealing or ultrasonic sealing.

This invention is applicable not only to the diaper of open-type but also to a diaper of pants-type having its front and rear waist regions previously connected to each other.

The disposable diaper according to this invention is primarily characterized in that contraction of the first elastic member causes the transversely opposite side edge regions of the supplementary absorbent batt structure to be pulled nearer to the longitudinal center line of the diaper, resulting in the distal end portion of the batt structure curving so as to delineate a circular arc which is convex upward with the body facing surface of the basic absorbent batt structure. With this diaper, the pocket with a large opening from the front waist region toward the crotch region is formed between these batt structures. This pocket has a sufficiently large receiving capacity for feces to prevent any significant quantity of feces from leaking out onto the latter batt structure and therefore there is no anxiety that any quantity of feces might cling to a wearer's skin.

With the diaper according to another embodiment, the transversely opposite side edge portions of the basic absorbent batt structure and the transversely opposite side edge portions of the supplementary absorbent batt structure are pulled nearer to the longitudinal center line as the first elastic member contracts. As a result, the zone of the basic absorbent batt structure underlying the distal end portion of the latter batt structure curved downward with respect to the lower surface of the latter batt structure while the distal end portion of the latter batt structure curves upward with respect to the body facing surface of the former batt structure. The pocket formed according to this alternative embodiment can offer an open space much larger than the pocket obtained by the embodiment in which only the latter batt structure curves upward with respect to the body facing surface of the former batt structure.

With the diaper arranged so that the supplementary absorbent batt structure has the absorbing capacity of bodily discharges higher than that of the basic absorbent batt structure, most of urine is absorbed and retained therein and prevents any quantity of the urine once absorbed in the supplementary absorbent batt structure from migrating into the pocket and being mixed with feces within the pocket.

With the diaper having, in addition to the basic and supplementary absorbent batt structure a second supplementary absorbent batt structure, contraction of the second elastic member causes a transversely opposite side regions of the third core to be pulled nearer to the longitudinal center line so that the distal end portion of the second supplementary absorbent batt structure curves upward with respect to the body facing surface of the basic absorbent batt structure. As a consequence, a pocket with a sufficient opening from the rear waist region toward the crotch region is formed between the basic and second supplementary absorbent batt structures to receive feces and thereby to prevent any quantity of feces from leaking out sideways beyond the end flaps in the rear waist region. With this diaper, there is no anxiety that any quantity of feces might cling to a wearer's skin in the front waist region as well as in the rear waist region.

The diaper according to still another embodiment having also, in addition to the basic and two supplementary absorbent batt structures, contraction of the second elastic member causes the transversely opposite side edge regions and the transversely opposite side edges of the second supplementary absorbent batt structure to be pulled nearer to the longitudinal center line of the diaper. As a consequence, the zone of the basic absorbent batt structure underlying the distal end portion of the second supplementary absorbent batt structure curves downward with respect to the lower surface of the second supplementary absorbent batt structure while the distal end portion thereof curves upward with the body facing surface thereof. The pocket formed according to this alternative embodiment can offer an open space much larger than the pocket obtained by the embodiment in which only the distal end portion of the second supplementary absorbent batt structure curves upward with respect to the body facing surface of the basic absorbent batt structure.

What is claimed is:

1. A disposable diaper comprising:
   a basic absorbent batt structure;
   at least one supplementary absorbent batt structure;
   said basic absorbent batt structure having a liquid-pervious body faceable surface and a liquid-impervious garment faceable surface, and a front waist region, a rear waist region and a crotch region;
   said supplementary absorbent batt structure having a liquid-pervious body faceable surface and an opposite lower surface, and a proximal end portion lying in said front waist portion and a distal end portion lying in said crotch region, and being placed upon the body faceable surface of said basic absorbent batt structure, the distal end portion terminating in a free end;
   an elastic member under an extension in a transverse direction extending in said transverse direction across the diaper, having transversely opposite end portions connected to side edge portions of said basic and supplementary absorbent batt structures, and having opposing surfaces that extend between said opposite end portions, the elastic member being positioned between the supplementary batt structure and the basic absorbent batt structure and being spaced from said free end in a zone of said distal end portion and adjacent said proximal end portion; and
   contraction of said elastic member causing the side edge portions of said supplementary absorbent batt structure to be pulled nearer to a longitudinal center line of said diaper so that said distal end portion of said supplementary absorbent batt structure curves so as to delineate a circular arc which is convex upward with respect to the body faceable surface of said basic absorbent batt structure and consequently a pocket opening from said front waist region toward said crotch region is formed between said basic and supplementary absorbent batt structures, said contraction causing each of said opposing surfaces of the elastic member to be spaced from said supplementary absorbent batt structure and said basic absorbent batt structure.

2. A disposable diaper according to claim 1, wherein said basic absorbent batt structure comprises a liquid-permeable topsheet, a liquid-impermeable backsheet and a liquid-absorbent first core disposed therebetween.

3. A disposable diaper according to claim 1, wherein said supplementary absorbent batt structure comprises a liquid-absorbent second core and a liquid-permeable sheet covering said second core.

4. A disposable diaper according to claim 1, wherein contraction of said elastic member causes side edge regions of said basic absorbent batt structure to be pulled nearer to said longitudinal center line of said diaper so that a zone of said basic absorbent batt structure underlying said distal end portion of said supplementary absorbent batt structure curves downward with respect to the lower surface of said supplementary absorbent batt structure.

5. A disposable diaper according to claim 1, further including
   a second supplementary absorbent batt structure having a body faceable surface and an opposed lower surface and lying on the body faceable surface of said basic absorbent batt structure so as to extend from said rear waist region toward said crotch region, said second supplementary absorbent batt structure comprising a proximal end portion lying in said rear waist region and a distal end portion lying in said crotch region so as to extend in said longitudinal direction, the distal end portion terminating in a free end, and
   a second elastic member under an extension in said transverse direction extending in said transverse direction across the diaper, having transversely opposite end portions substantially connected to the side edge portions of said basic and second supplementary absorbent batt structures, and having opposing surfaces that extend between said opposite end portions, the second elastic member being positioned between the second supplementary batt structure and the basic absorbent batt structure and being spaced from said free end of said second supplemental batt structure, in a zone of said distal end portion and adjacent said proximal end portion; wherein
   contraction of said second elastic member causes side edge portions of said second supplementary absorbent batt structure to be pulled nearer to said longitudinal center line so that said distal end portion of said second supplementary absorbent batt structure curves upward with respect to the body faceable surface of said basic absorbent batt structure and consequently a pocket opening from said rear waist region toward said crotch region is formed between said basic and supplementary absorbent batt structure, said contraction causing each of said opposing surfaces of said second elastic member to be spaced from said second supplementary absorbent batt structure and said basic absorbent batt structure; and said distal end portions of said two supplementary absorbent batt structures are spaced from each other by a predetermined dimension in said longitudinal direction so that the body faceable surface of said basic absorbent batt structure is exposed between said distal end portions of said two supplementary absorbent batt structures.

6. A disposable diaper according to claim 5, wherein contraction of said second elastic member causes the side edge regions of said basic absorbent batt structure to be pulled nearer to said longitudinal center line of said diaper so that a zone of said basic absorbent batt structure underlying said distal end portion of said second supplementary absorbent batt structure curves downward with respect to the lower surface of said second supplementary absorbent batt structure.

7. A disposable diaper according to claim 5, wherein a dimension by which said supplementary absorbent batt structure extends from said front waist region to said crotch region is larger than a dimension by which said second supplementary absorbent batt structure extends from said rear waist region to said crotch region so that the body faceable surface of said basic absorbent batt structure is exposed in a zone of said crotch region nearer to said rear waist region.

8. A disposable diaper according to claim 1, wherein an absorbing capacity for body discharges per unit area of said supplementary absorbent batt structure is greater than that of said basic absorbent batt structure.

* * * * *